United States Patent [19]

Callaghan et al.

[11] Patent Number: 4,858,610
[45] Date of Patent: Aug. 22, 1989

[54] DETECTION OF CARDIAC EVOKED POTENTIALS

[75] Inventors: Frank J. Callaghan, Miami; Edward A. Schroeppel, Miramar, both of Fla.

[73] Assignee: Telectronics, N.V., Antilles, Netherlands

[21] Appl. No.: 157,084

[22] Filed: Feb. 8, 1988

Related U.S. Application Data

[63] Continuation of Ser. No. 807,547, Dec. 11, 1985, abandoned.

[51] Int. Cl.$^4$ ............................................. A61N 1/36
[52] U.S. Cl. .............................................. 128/419 PG
[58] Field of Search ......... 128/419 P, 419 PG, 419 D

[56] References Cited

U.S. PATENT DOCUMENTS

| | | | |
|---|---|---|---|
| 3,478,746 | 11/1969 | Greatbatch | 128/419 PG |
| 4,055,189 | 10/1977 | Auerbach et al. | 128/419 PG |
| 4,091,817 | 5/1978 | Thaler | 128/419 PG |
| 4,114,627 | 9/1978 | Lewyn et al. | 128/419 PG |
| 4,310,000 | 1/1982 | Lindeman | 128/419 PG |
| 4,344,437 | 8/1982 | Markowitz | 128/419 PG |
| 4,387,717 | 6/1983 | Brownlee et al. | 128/419 PG |
| 4,532,931 | 6/1985 | Mills | 128/419 PG |
| 4,535,776 | 8/1985 | Strandberg et al. | 128/419 PG |
| 4,549,548 | 10/1985 | Wittkampf et al. | 128/419 PG |
| 4,579,119 | 4/1986 | Callaghan | 128/419 PG |

FOREIGN PATENT DOCUMENTS 2119255  11/1983  United Kingdom.

OTHER PUBLICATIONS

European Pat. Appln. #0057944 Publ., Aug. 18, 1982, to Wittkampf et al.
European Pat. Appln. #00033418 Publ. Aug. 12, 1981, to Funke et al.

*Primary Examiner*—Francis Jaworski
*Attorney, Agent, or Firm*—Gerstman & Ellis, Ltd.

[57] ABSTRACT

Automatic detection of cardiac pacer evoked potentials may be obtained through a cardiac pacer lead positioned in a heart chamber. An electrical stimulus is emitted in unipolar mode from a first electrode to stimulate muscular contraction. The cardiac electrical activity evoked by the stimulus is then detected in unipolar mode by a second electrode which is spaced from the first electrode and free of electrical connection thereto. Accordingly, signal interference caused by residual polarization of the first electrode is suppressed. The natural cardiac electrical activity is sensed in a bipolar mode, and the pulse is inhibited if a heartbeat is detected within an alert period.

40 Claims, 8 Drawing Sheets

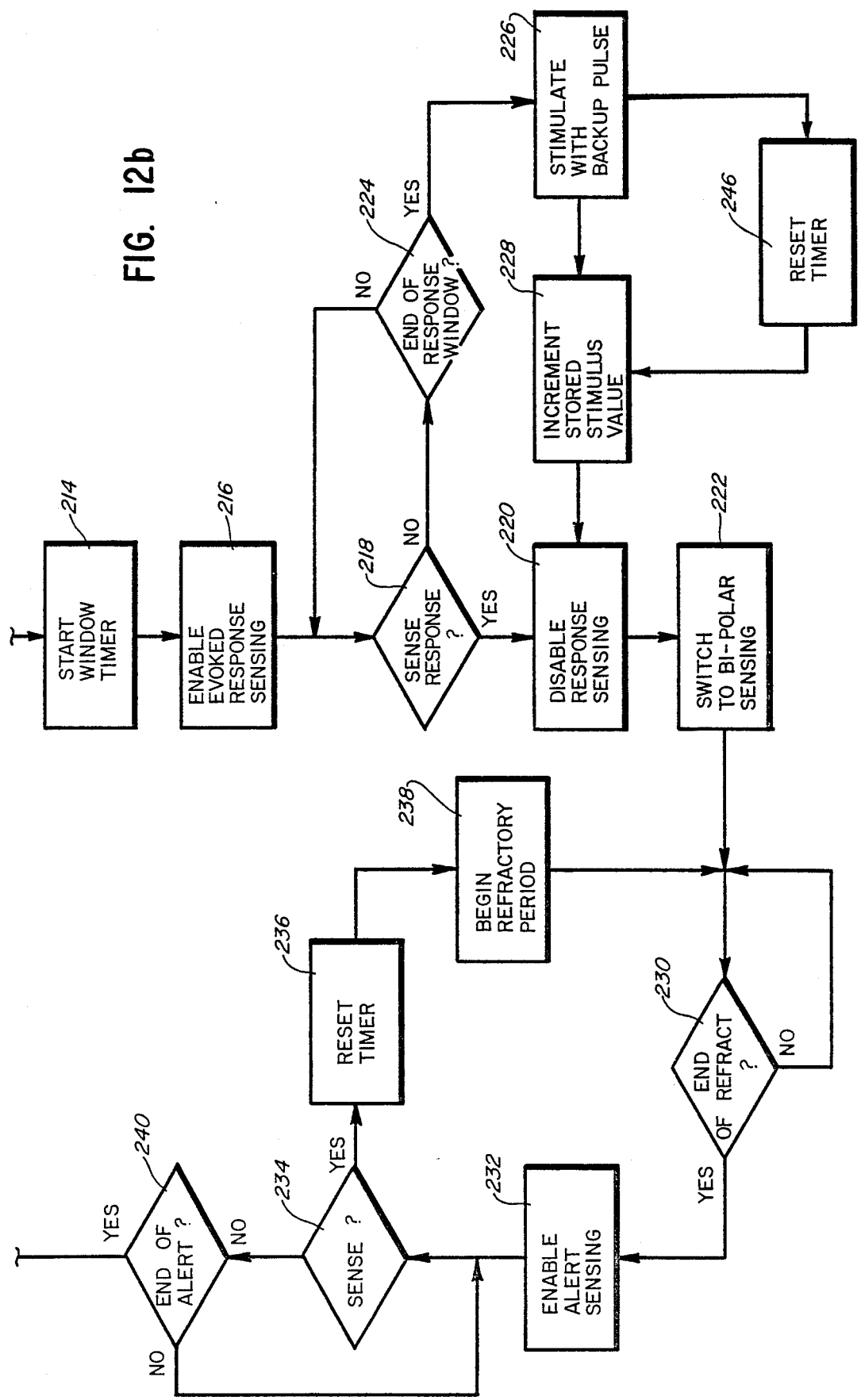

DETECTION OF CARDIAC EVOKED POTENTIALS

This application is a continuation of U.S. application Ser. No. 807,547, filed Dec. 11, 1985, and now abandoned.

BACKGROUND OF THE INVENTION

An implantable cardiac pacer can have various pacing modes as well as various output parameters such as rate, output level (current or voltage, pulse duration or both), sensitivity, refractory period, etc. In some cardiac pacers both the mode, e.g. R-wave inhibited VVI, as well as the various output parameters, are preset during production, whereas in other cardiac pacers either mode or output parameters or both can be altered by external control or programming. Such output parameters and/or pacing mode changes are usually accomplished by the attending physician, usually during an office visit. Therefore, such cardiac pacers may not be responsive to the physiological requirements of the patients. Such requirements fluctuate often during a 24 hour period, certainly more frequently than the interval between patient's visits to the physician. Thus the patient must suffer less than optimum heart pacing.

Increased emphasis is being placed on the use of physiological parameters to control the output parameters, and particularly the rate of stimulation, of implantable cardiac pacers. Such physiological parameters can include activity of the patient (Dahl, U.S. Pat. No. 4,140,132), sensed ionic changes (Wirtzfeld, U.S. Pat. No. 4,202,339) and the stimulus-repolarization interval of the T-wave, (Richards, U.S. Pat. No. 4,228,803). The detection of such changes is utilized either to increase or to decrease the rate of stimulation.

Measurement of physical activity or of the ionic level in the blood does not appear to measure the effectiveness of the pulse emitted from the cardiac pacer initiating myocardial contraction, nor do they permit analysis of the evoked potential, which is generated by the contracting heart. In addition, these do not consider the sympathetic and parasympathetic contributions to cardiac activity. However, measurements of the stimulus to T-wave intervals or repolarization potential does give an indication of effectiveness of stimulation. Absence of repolarization would indicate lack of stimulation; i.e. the heart failed to contract. However, the use of this repolarization to regulate output level (output current or voltage, output pulse duration, or both) could cause delay and irregularity in myocardial contraction or heart rate which the patient may feel.

Detection of the depolarization potential which must, by necessity, precede repolarization can give more immediate information on the presence or absence of effective stimulation within a sufficiently short period of time to permit the resulting intervals between ventricular contractions to be made essentially equal by appropriate stimulating pulse generation.

In order to utilize the presence or absence of the depolarization potential or R-wave, to decrease (or increase) the output level of the cardiac pacer, one must detect the R-wave. When the same electrodes are used to generate pulses to stimulate muscle contraction and to record the resulting depolarization, the detected depolarization is markedly reduced, because it is masked or buried in the exponential decay of the polarization charge on the electrode resulting from the stimulus itself.

In Herscovici, U.S. Pat. No. 4,543,956, issued Oct. 1, 1985, there is described a means for dissipating the polarization charge on the stimulating electrode. Stimulation and sensing of the resulting R-wave is accomplished by the same electrode. The polarization charge is dissipated by the use of a biphasic pulse in which the first phase is of shorter duration and greater amplitude, stimulating the myocardium. The second phase is of the opposite polarity, of lower amplitude and of longer duration than the first. When the polarization charge equals zero i.e. when no net charge is delivered, the second phase of the biphasic pulse drops to zero, and the evoked potential sensing amplifier is triggered into the "on" state.

The present invention pertains to a cardiac pacing system which preferably combines the unipolar and bipolar configuration. It typically uses a bipolar lead which may be placed in the atrium or the ventricle, or a pair of bipolar leads, one in the ventricle and one in the atrium for dual chamber pacing. The invention further pertains to a method of discrimination of the cardiac evoked potential from post stimulus electrode polarization. When the evoked potential is detected, its amplitude and/or configuration can be utilized to regulate automatically, with minimal external control, the implantable cardiac pacer's output characteristics. Thus the pacer itself can regulate the heartbeat in a more naturally physiological manner.

DESCRIPTION OF THE INVENTION

In a method of cardiac pacing and sensing one provides a cardiac pacing lead positioned in a heart chamber. One periodically emits an electrical stimulus from a first electrode which is preferably carried on the distal end of the lead, to stimulate muscular contraction of a portion of the heart. One then detects an electric cardiac response evoked by said stimulus, indicating said muscular contraction, by a second electrode carried by the lead, which is spaced from the first electrode, and free of electrical connection thereto at the time the evoked response is being sensed. As the result of this, signal interference caused by residual polarization of the first electrode is diminished, to reduce its interference with the sensing of an evoked response by the second electrode, since the second electrode is isolated from the first electrode.

Preferably, the second electrode is spaced from the first electrode by at least about 0.5 cm., with the second electrode being in the form of a ring positioned about the cardiac pacing lead.

Additionally, the pacer lead connects to pacer power and circuit means, which may preferably be sealed in a metal can, the metal can serving as a reference electrode to the first and second electrodes during the electrical stimulus emitting and the evoked response sensing phases.

Alternatively, a third electrode, typically but not necessarily adjacent to the pacer power and circuit means, may be used as the reference electrode, for example in an instance where the pacer power and circuit means are sealed in a non-conductive plastic casing or the like, or it is desired simply not to use the metal can as a reference electrode because the metal can, when utilized as a reference, may retain some polarization charge.

To further reduce the effect of residual polarization of the first electrode, following generation of each pulse by the first electrode, an output capacitor which is in electrically conductive relation with the first electrode may be discharged through the heart for typically 5 to 15 milliseconds, to cause residual charge to depart the first electrode.

The evoked response sensing circuit including the second electrode and described above may have additional circuitry for activating it at a predetermined time interval after the pulse of electric potential, the duration of such activation being typically about 10 to 50 milliseconds, to provide a window of sensed response covering the time at which the evoked response should be sensed if it takes place. By providing a relatively short time window of response for detecting the evoked response, the system becomes more discriminating toward detecting the actual cardiac evoked response during that period when it is most likely to occur. Accordingly, the evoked response can be detected and selected.

As a further feature of this invention, at a predetermined interval before the pulse of electrical stimulus is emitted, and while the evoked response sensing circuit is not operating, a circuit may be activated including said first and second electrodes in bipolar relation to identify heart electrical activity associated with heartbeat generation. Upon sensing of such heart electrical activity, the emission of the electrical stimulus from the first electrode may be inhibited, and the natural signal can cause the heart muscle to contract in normal manner.

Typically, the predetermined interval before the electrical stimulus discussed herein may be positioned after the evoked response sensing window has closed, but prior to the time of the next electrical stimulus. It is known as the "alert period", and follows a refractory period during which naturally occurring electrical activity cannot be detected by apparatus using the first electrode.

Among other designs which may be used, it may be desired to provide a multiple cardiac pacing lead in which pairs of first and second electrodes are carried on separate lead sections, typically two or more of such sections. The electrode pairs are all in electrical communication with the pacer and power circuit means. As stated before, a metal can may be provided enclosing the power circuit means for protection thereof, and also to serve as an opposite electrode to the first and second electrodes, but alternatively a separate, third electrode may be used for that purpose. One of the pairs of electrodes on one lead section may be for atrial installation, while another pair on another lead section may be for ventricular installation.

It is preferred that the first electrode emits its electric stimulus in the unipolar mode. Similarly, the second electrode preferably detects the electric response evoked by such stimulus in the unipolar mode. However, the first and second electrodes preferably operate together during the alert period preferably in the bipolar mode, this period being positioned in time between the closing of the window of evoked potential sensing and the subsequent emission of an electric stimulus from the first electrode. However, unipolar sensing is also possible. Alternatively, a single lead may be used having four electrodes: two end electrodes (tip and ring) for the ventricle and two ring electrodes, spaced from the end, for the atrium.

The electrogram of the evoked electric response may be telemetered out to a recording device external to the patient for analysis if desired, or for storage of the electrogram within the pacer for later telemetering.

DESCRIPTION OF THE DRAWINGS

FIGS. 12a–12b, when connected together, comprise a flow chart depicting an operation of the diagram of FIG. 11.

DESCRIPTION OF SPECIFIC EMBODIMENTS

Figure 1:
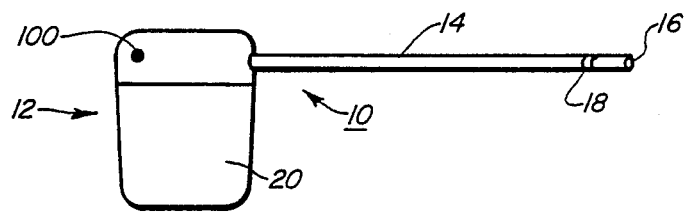
FIG. 1 is an elevational view of a cardiac pacing system with a bipolar lead which functions both as a unipolar and a bipolar system at different steps of the operating cycle.

Referring to the drawings, in FIG. 1 a single chamber cardiac pacing system 10 includes pulse generator 12, which may be of generally conventional electronics except as otherwise described herein. Pervenous bipolar lead 14 is also provided and may be of conventional bipolar pervenous or epicardial design.

First electrode 16 may be a porous, platinum-iridium, hemispherically shaped electrode on the distal end of lead 14, communicating with a metal conductor inside of the lead. Ring electrode 18 serves as a second electrode, being capable of electrical isolation by means of the circuitry and pulse generator 12 from first electrode 16, and being typically spaced at least 0.5 cm. from first electrode 16. Second, ring shaped electrode 18 may be also made of the same alloy and may communicate with its own circuit wire within lead 14, and may or may not be porous-coated.

The circuitry of pulse generator 12 may be sealed in a hermetic container, for example titanium can 20, as shown.

Cardiac pacing system 10 may be external or surgically installed into the patient, and may operate to pace the patient's heart as follows.

When the pacer can 20 is treated as an independent electrode, the single chamber cardiac pacing system 10 carries three electrodes; can 20, first electrode 16, and second electrode 18. The operation of the pacing system as described applies to both the atrial and ventricular leads of a dual chamber cardiac pacer or an atrial standby pacer. However, for purposes of simplicity of disclosure, the details of operation will be described for a ventricular asynchronous pacer (VOO) or a ventricular inhibited demand pcer (VVI).

A pacing cycle begins when a physiologic electric stimulus is emitted from first electrode 16 to stimulate muscular contraction of at least a portion of the heart. The stimulus is of a magnitude and duration which is not harmful to the heart and which is well known to those skilled in the art to evoke a contraction response from the heart muscle. The pulse of electric stimulus 30 is graphed in FIG. 4 at channel A, having a typical duration of 0.1 to 2 milliseconds.

Figure 5:
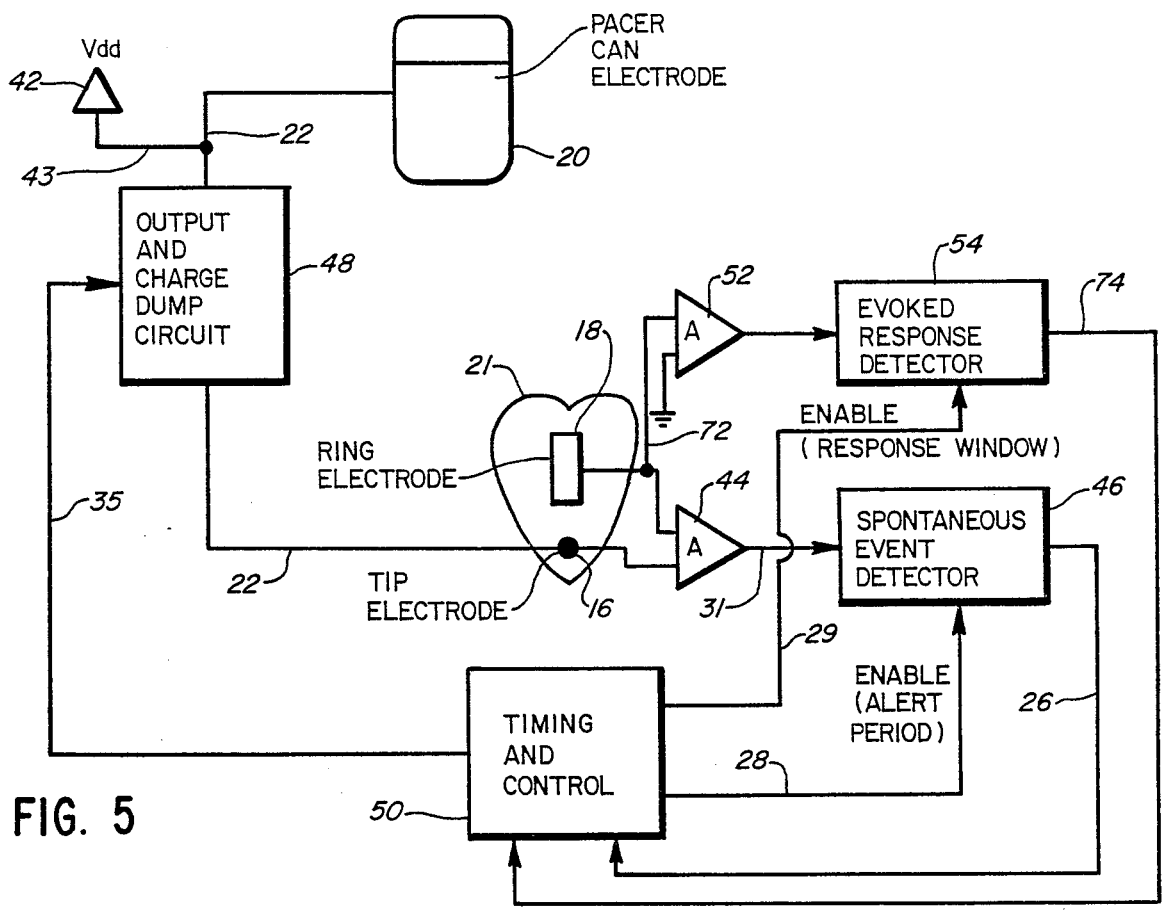
FIG. 5 is a schematic block diagram of a single chamber cardiac pacer with evoked potential monitoring in accordance with this invention.

Referring to the circuit of FIG. 5, pacer can 20 is shown serving as a reference electrode for electrodes 16, 18, carried at the heart 21 which is shown in schematic manner. Stimulus 30 passes through conductor 22 to be emitted from tip electrode 16. The naturally occurring cardiac electrical activity is amplified by amplifier 44 and transmitted via line 31 to a spontaneous event detector 46 to begin a timing process. The signal proceeds via conductor 26 into timing and control circuitry module 50 which, in turn, has feedback and control wires 28, 29 connected, respectively, to detector 46 and to evoked response detector 54. Likewise an output from timing and control circuit 50 is connected via line 35 to output and charge dump circuit 48.

Figure 4:
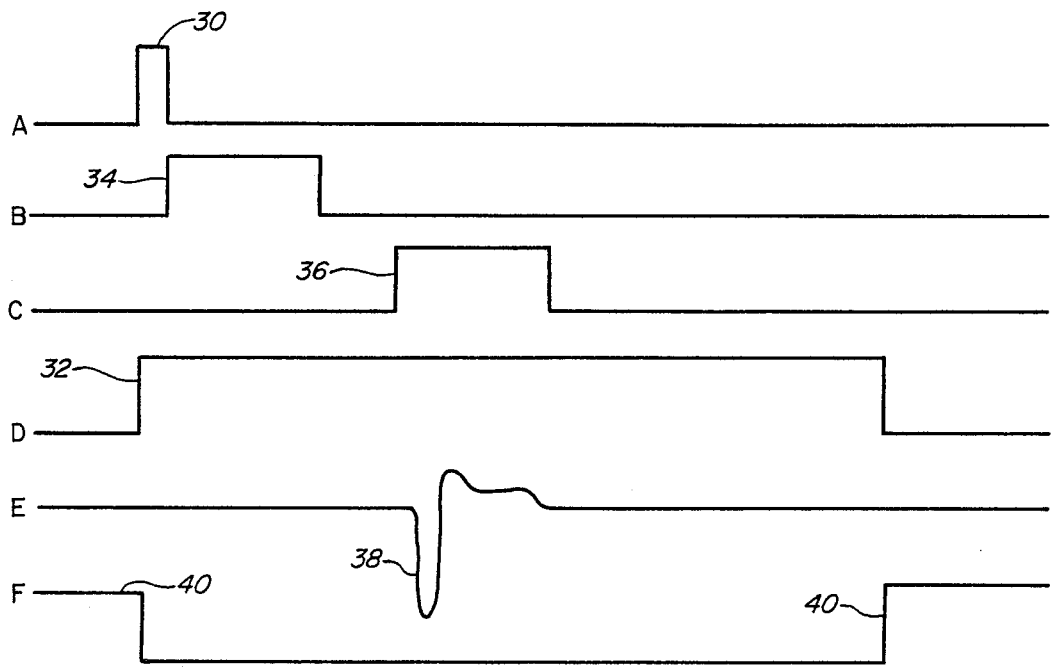
FIG. 4 is a timing diagram of the relationship of the electronic events which take place during a single cycle in accordance with this invention.
Figure 6:
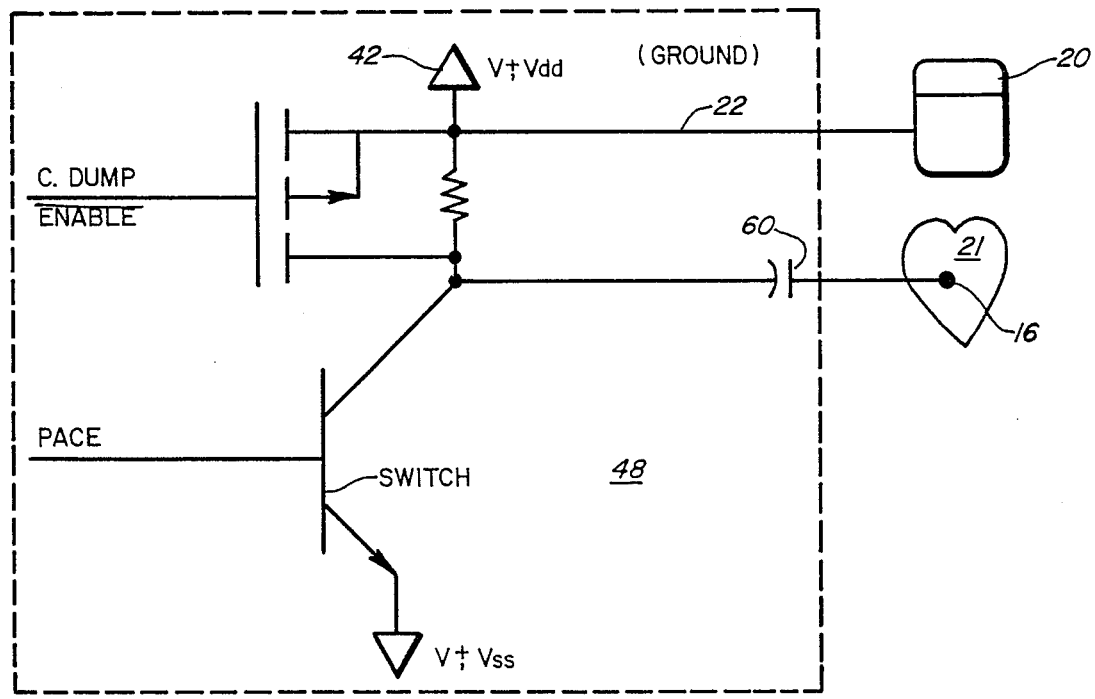
FIG. 6 is a schematic block diagram of the charge dump circuit used in the device of FIG. 6.

Immediately following the emission of pulse 30 from electrode 16, charge dump circuit 48 is activated, with the charge dump pulse 34 being illustrated on channel B of FIG. 4, the duration of the charge dump being about 5 to 15 milliseconds. The charge dump may be provided using a conventional charge dump circuit 48 such as illustrated in FIG. 6. During the charge dump period, the electrical charge on output coupling capacitor 60 (FIG. 6) and first electrode 16 are discharged through the heart 21. Thus the post-stimulus polarization potential of electrode 16 is quickly diminished.

Evoked response detector 54 is then activated by timing and control circuit 50 through conductor 29. A window of time 36 is opened as illustrated in channel C of FIG. 4, its duration being typically 10 to 50 milliseconds. It is only during this time that evoked response detector 54 is activated to detect an evoked electrical response coming from the heart and to indicate a contractile response to the physiological pulse of electric potential 30.

The stimulus from electrode 16 can be seen to be in the unipolar mode. Likewise, detection of the evoked response is unipolar, being detected by electrode 18, which communicates through conductor 72 to amplifier 52, which sends the amplified signal to detector 54. When an evoked response is detected, detector 54 may signal timing and control circuitry 50 through line 74 for further timing of the system.

It is noted that the window of time 36 on channel C of FIG. 4 is positioned in a block of time 32 (channel D of FIG. 4) which generally represents a refractory period in which first electrode 16 may not be used to sense any electrical activity. By this invention, it can be seen that the evoked response can be detected during such a refractory period.

Channel E in FIG. 4 shows the evoked cardiac electrical activity 38 within evoked response detection period 36, and which is detected by second electrode 18. It can be seen that the detection of evoked heartbeat response 38 is detected by second electrode 18 in the unipolar mode. The detected evoked response is sent through conductor 74 to timing and control circuit 50, and may serve to set the timer to zero for timing the next physiological pulse to be emitted from first electrode 16.

However, there is a need to determine that natural heartbeats will not show up at unexpected times, to avoid the result where the pacing system disrupts and interferes with the natural heartbeat. To this end, beginning essentially at the end of refractory period 32, during which event detector 46 is disabled from sensing electric pulses, an alert period 40 is provided to monitor a naturally occurring cardiac electrical activity until such time as the next pulse 30 is sent out through first electrode 16. Alert circuitry 46 may be activated and shut down by timing and control circuit 50 through conductor 28. When the alert phase 40 is in operation, both electrodes 16 and 18 are operating together in a bipolar mode, with both electrodes communicating with amplifier 44, which in turn is connected to spontaneous event detector 46.

In the event of a spontaneous heartbeat, a signal may be sent from spontaneous event detector 46 via line 26 to timing and control circuit 50, to cause the electronics to recycle from any time in the cycle to the beginning of the cycle, without generation of an electric pulse 30 from first electrode 16. Every time natural cardiac electrical activity takes place during alert period 40, no electric pulse 30 will be generated.

In the event, however, that detector 46 does not detect natural cardiac electrical activity during the alert period, timing and control circuitry will cause another electric pulse 30 to be generated via electrode 16.

Figure 7:
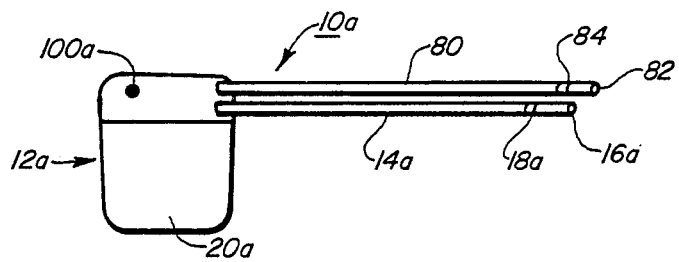
FIG. 7 is an elevational view of a dual chamber pacing system, each chamber having a bipolar lead, each bipolar lead functioning both as a unipolar and a bipolar system at different phases of the cycle of operation.

Turning to FIG. 7, a cardiac pacer system 10a is provided, having pacer circuitry 12a enclosed in a metal can 20a of the type similar to FIG. 1. Pacer lead 14a carries similar electrodes 16a, 18a, similar to the electrodes of the previous embodiment.

However, an additional pacer lead 80 is provided, carrying first electrode 82 and second electrode 84 similar to first and second electrodes 16, 18, or electrodes 16a, 18a. Lead 14a may be positioned in a ventricle of a heart, while lead 80 is positioned in the atrium.

The functioning of the individual leads 14a, 80 of pacer 10a is closely analogous to the functioning of lead 14 and its electrodes in the embodiment of FIG. 1, with the same steps being used for providing the electric pulse via either of electrodes 16a, 82, sensing the evoked response with second electrodes 18a, 84 within a predetermined time window, and then timing the next electric pulse from first electrodes 16a, 82 from the evoked response, unless, during an alert period where the respective first and second electrodes are operating together in bipolar mode, an electric signal of a natural heartbeat is detected.

The charge dump circuit 48 may be used with each of the leads of this second embodiment, in a manner similar to its optional use in the first embodiment. Such a charge dump on the electrode alleviates the cathodal polarization on that electrode to avoid a "near field" signal to the second electrode. In other words, the second electrode, relative to the can 20 or 20a, operating as a reference electrode, can detect the polarization of the tip, which can decrease the evoked response signal when no charge dump occurs.

Furthermore, when can 20, 20a is used as a reference electrode, it has large surface area, low stimulation current density, and low post-stimulus polarization potential. The pacer can serves as the anode at Vdd and is a reference for the unipolar single-ended amplifier. The cardiac pacer can 20, 20a may be connected to the positive side of the battery.

Because second electrodes 18, 18a, 84 are slightly removed from the pulse site of the first electrodes, there is a physiological propagation delay between stimulation and the arrival of the cardiac excitation wave front at each second electrode. This delay allows more time for the polarization recovery of the second electrode, as needed, dependent upon the magnitude of the pulse, the distance between the first and second electrodes, and the myocardial conduction velocity.

Figure 2:
FIG. 2 is a diagram showing how the evoked potential may be masked by exponential decay of the pacer pulse when one attempts to sense the evoked potential from the electrode which emits the pacer pulse.

Referring now to FIG. 2 an electrographic tracing of the physiologic pulse provided by the first electrode is shown, in which the evoked response 38 is attempted to be monitored from a first electrode. It can be seen that the evoked response 38 is barely visible, being masked by the exponential decay 39 of the polarization of the first electrode.

Figure 3:
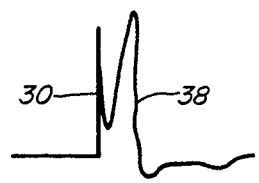
FIG. 3 is a diagram of the evoked potential as it may be detected in accordance with this invention.

Now, turning to FIG. 3, this electrogram is taken from the second electrode in accordance with this invention. Stimulus pulse 30 is shown, and a second pulse 38 is shown, which is the evoked response. Thus it can be seen that an evoked response can be detected with great ease in accordance with this invention.

Hence, a cardiac pacing system is provided, which functions during its cycle as both a bipolar and a unipolar system depending upon a particular moment-by-moment function in the cycle. In the bipolar mode, when electrical activity indicative of naturally-occurring cardiac activity is being sensed, the system exhibits good immunity from electromagnetic interference, freedom from myopotential inhibition, good rejection of far-field cardiac events, good rejection of post-stimulus polarization potentials, and true differential sensing with a remote reference.

However, in the unipolar mode, such as during the time of evoked response sensing window 36, the electrocardiographic interpretation is easier due to a prominent stimulus artifact. Also, a large anode such as metal can 20 or 20a may be provided to reduce polarization. Likewise, anodal cross-stimulation is avoided, and there is no need for isolated output stages.

Finally, the use of the second ring electrode 18, 18a, 84 in unipolar mode can be used with a charge dump if needed to reduce polarization of the second ring electrode to a sufficient degree for good sensing of an evoked response. Likewise the system works with available linear bipolar electrodes, so that no design change from currently available bipolar cardiac leads is required. Verification of capture on a beat-by-beat basis is provided, with a wide safety margin. One may also determine if an exit block occurs at the stimulation site with automatic control of the stimulus parameter via capture search, and threshold tracking circuitry may be used. Likewise, the apparatus of this invention enables a rate response function which is based on the ventricular evoked response. Thus the heart rate may be controlled in a manner which is natural and desirable.

If desired, a separate electrode 100, 100a may be used as the reference electrode anode in either of the pacer systems 10, 10a rather than the metal cans 20, 20a. Such a reference electrode may also be an additional ring on lead 14, if desired.

Figure 8:
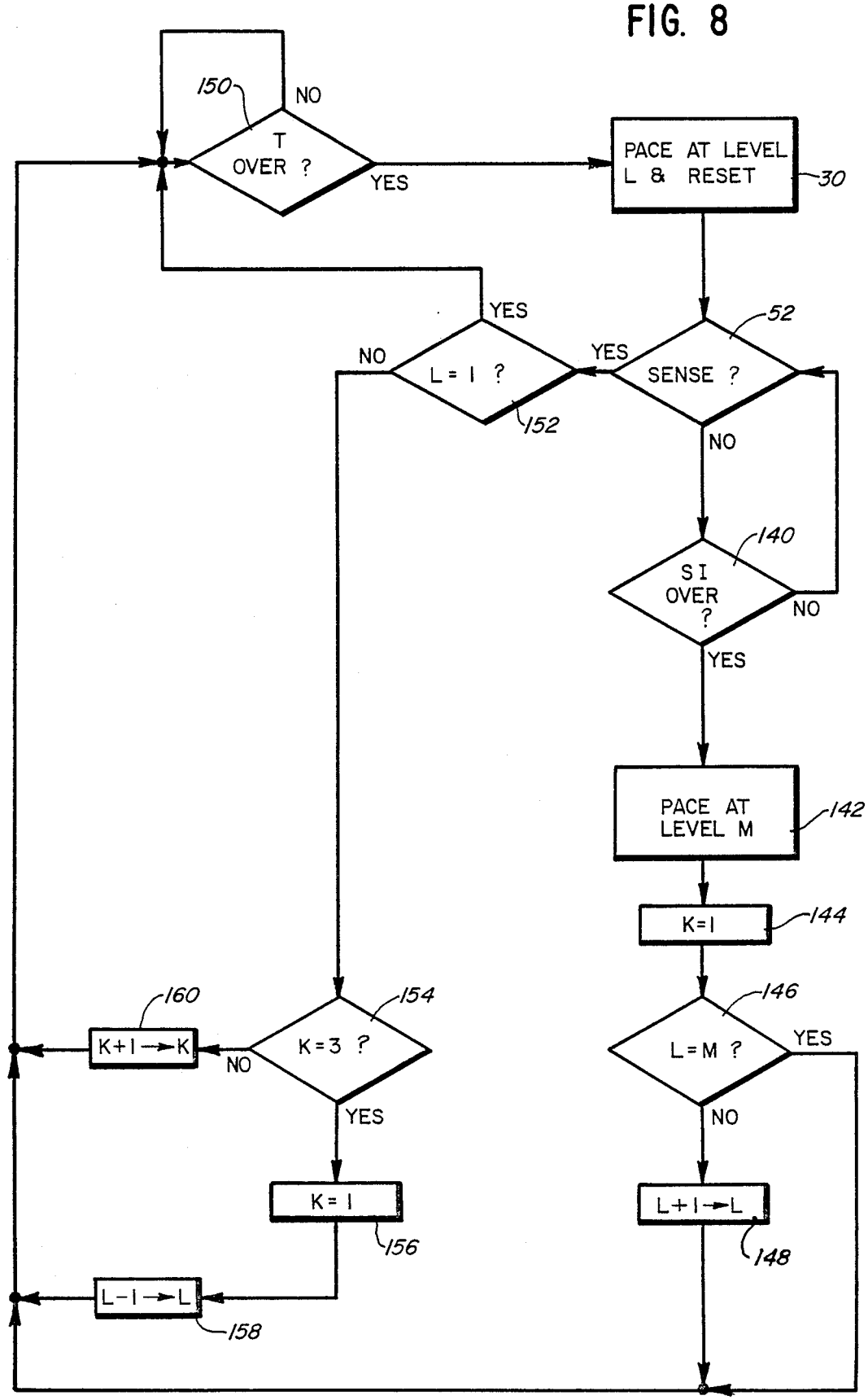
FIGS. 8, 9, and 10 are flow charts, showing three different ways in which the invention of this application may be utilized in a computer-aided process.

FIG. 8 is a flow chart showing pacer operation in one embodiment. Pacer 12 emits an output pulse 30 from electrode 16 (FIG. 1). Output pulse 30 activates the evoked response sensing amplifier 52 (FIG. 5) for a sensing interval of typically less than 50 milliseconds (140-FIG. 8). At the end of the sensing interval, if no evoked response was detected, the cardiac pacer emits a stimulus at the maximum output level (142), and the pulse to pulse interval is reset. The counter is set to 1 (144).

Furthermore, if the output level is not at its maximum level 146, the existing output level is increased to its next higher output level L+1→L(148). When the pulse to pulse interval T is complete, or the programmed duration of the pulse to pulse interval is complete, the cardiac pacer emits another pulse 30 from first electrode 16 at the output level as determined by logic units 146 or 148.

Again, the evoked response detector 54 is activated to detect evoked response 38. If the output level is at its lowest value L=1(152) nothing further is needed, and the pulse to pulse interval elapses (150). However, if the output level is not at its lowest value and there has been a total of three detected evoked responses (154) at that particular output level, the counter is reset to 1 (156), and the output level is decreased to the next lower level (158).

At the end of the programmed pulse to pulse interval (150), the cardiac pacer will stimulate the heart at the output level determined at 152 or 158. If, on the other hand, three evoked responses (or any predetermined number) have not been detected, counter (160) is incremented by 1, and the pulse-to-pulse timing continues.

Figure 9:
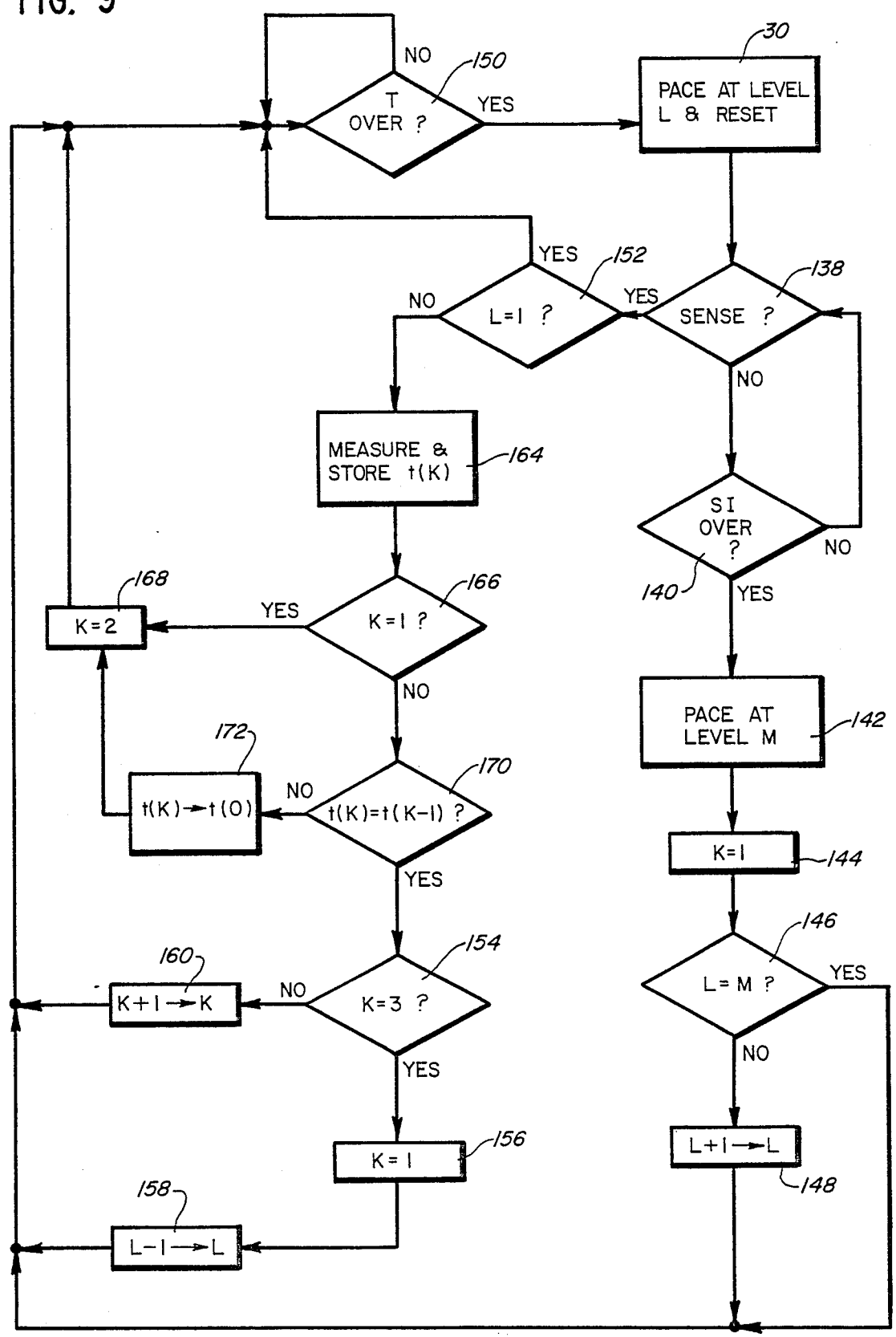

Referring now to FIG. 9, a second flow chart is disclosed showing the pacer operation of another embodiment. It can be seen that many of the steps are the same as in the previous embodiment of FIG. 8, the same steps carrying the same reference numerals; specifically, reference numerals 130 through 152 and reference numerals 154–160.

The added steps in FIG. 9 are based on the premise that evoked response to each stimulus occur at approximately equal intervals after stimulus, whereas in a non-evoked potential of electric stimuli from natural cardiac action, this interval tends to be more variable. Further, the output level (30) is changed after three evoked potentials have been detected in the sensing interval of the evoked response amplifier.

One determines (152) whether or not the output level is at its lowest programmed value. If it is not, the time interval t(k) is measured and stored (164). This time interval is a measured time within the less than 50 milliseconds in which the evoked potential may be detected.

Counter 166, if set at 1, proceeds to signal counter 168 to increment k to equal 2, and in this case the process proceeds to the end of programmed pulse-to-pulse interval, this being monitored (150) to determine the end of such interval.

However, if point 166 is not at 1, the interval sensed is compared to the prior sensed interval (170). If the two intervals are equal within a predetermined error range, and point 154 is at 3, then the series proceeds in the manner described in the previous embodiment of FIG. 8. However, if the interval sensed is not equal within predetermined limits, t(k) is decreased to time interval t(0) (172); counter 168 is made to equal 2, and the series proceeds as described in the previous embodiment of FIG. 8.

If, however, the two compared times (170) are equal, and k=3 as determined at counter 154, then k is made to equal 1 at counter 156; and the output level L is reduced by one unit (158) for the next emitted pulse 30 as timed at timing circuit 150.

Figure 10:
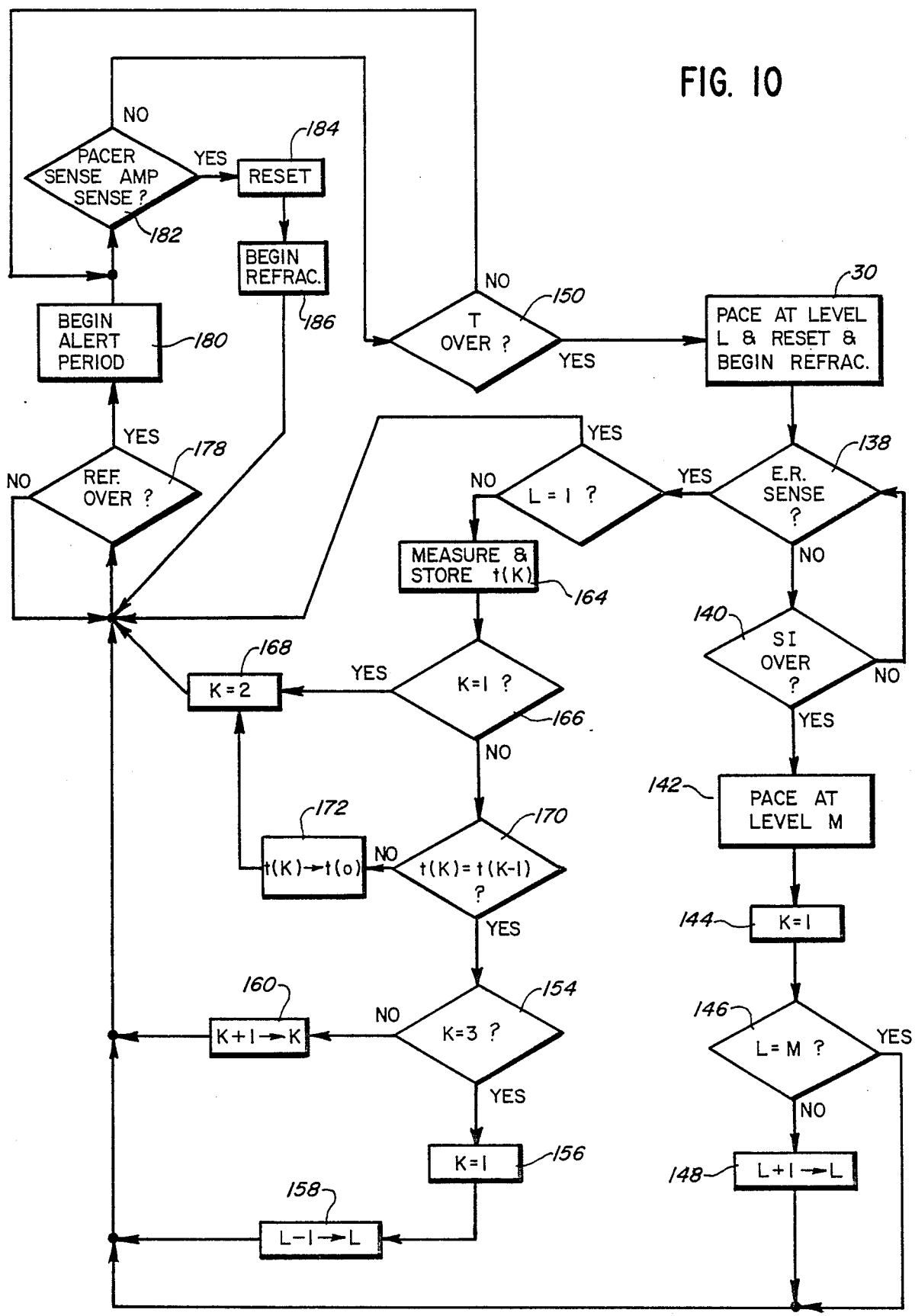

Turning to FIG. 10, it can be seen that the functions of FIG. 9 are still present, bearing the same reference numerals, but that added functions are also provided.

Basically, a pacing sensing amplifier 182 is added to the circuit so that naturally occurring electrical activity can be detected. In this system, the pulse-to-pulse interval is divided into a refractory period (186) and an alert period (180). The refractory period is the time that first electrode 16 cannot sense electric signals from the heart. The alert period is the time when naturally occurring electrical activity is sensed.

The heart electrical activity, when sensed during the alert period, initiates a new pulse-to-pulse interval.

The delivery of pulse 30 is unipolar. The sensing of the evoked ventricular activity is unipolar i.e. between the tip electrode 16 and the metal case 20 of the cardiac pacer, for example. However, the sensing of naturally occurring ventricular activity is bipolar, i.e. between the tip electrode 16 and the ring electrode 18.

In the FIG. 10 system, two different electrical events are being sensed; that which results from pulse 30, such evoked response occurring almost immediately after the pulse, and also that electrical activity which can occur by a non-induced heartbeat.

The system which detects the evoked response is the same as the previous embodiment. To this system are added steps to detect the electrical activity of spontaneous heart activity.

Pulse 30 activates the evoked response sensing amplifier and detector 52, 54 (FIG. 5) and naturally sets off the refractory period 32 (FIG. 4). The system determines the end of the refractory period (178). At the end of the refractory period, alert period 180 begins, at which time the sensing for spontaneous heart activity takes place. If such activity is sensed by amplifier 182, the programmed pulse-to-pulse interval is reset to zero (184), and the refractory period begins again (180). However, if no spontaneous activity is sensed (182) during the alert period, the timing completes its programmed interval (150), and another output pulse 30 is emitted from electrode 16, resetting the sensing interval for the evoked response and the refractory period.

Figure 11:
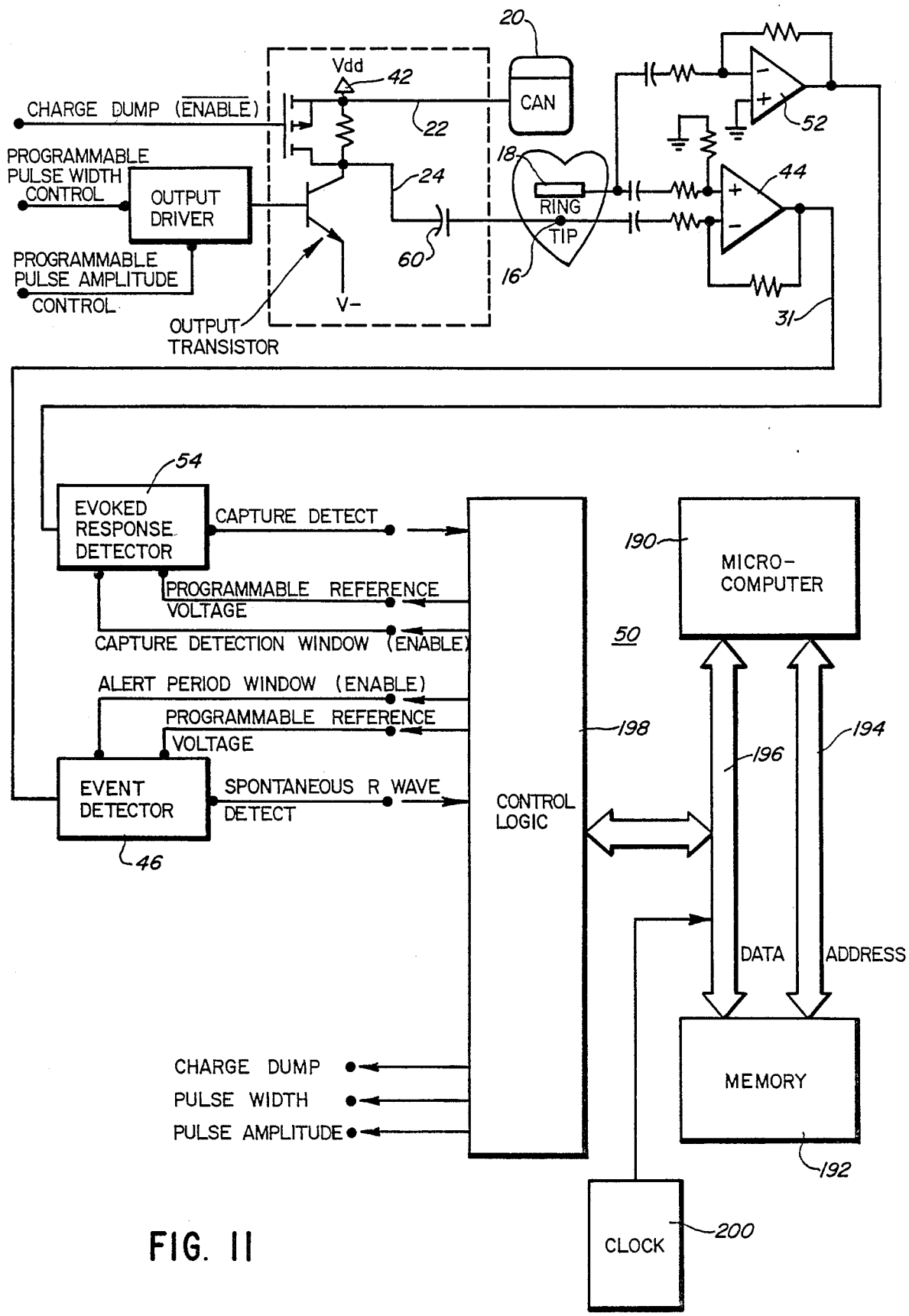
FIG. 11 is a schematic diagram of another embodiment of a pacer system constructed in accordance with the present invention.

A relatively detailed schematic diagram of the pacer electronics is presented as FIG. 11. Referring to FIG. 11, it is seen that the same reference numerals are used for the same components of FIG. 5. Timing and control circuit 50 comprises a microcomputer 190 which addresses a memory 192 via address bus 194. Data bus 196 is coupled between microcomputer 190 and memory 192, and conventional control logic 198 is coupled to data bus 196. A crystal controlled clock 200 is used for providing appropriate clock pulses for the system. The functions of the control logic inputs and outputs are designated on FIG. 11.

Figure 12A:
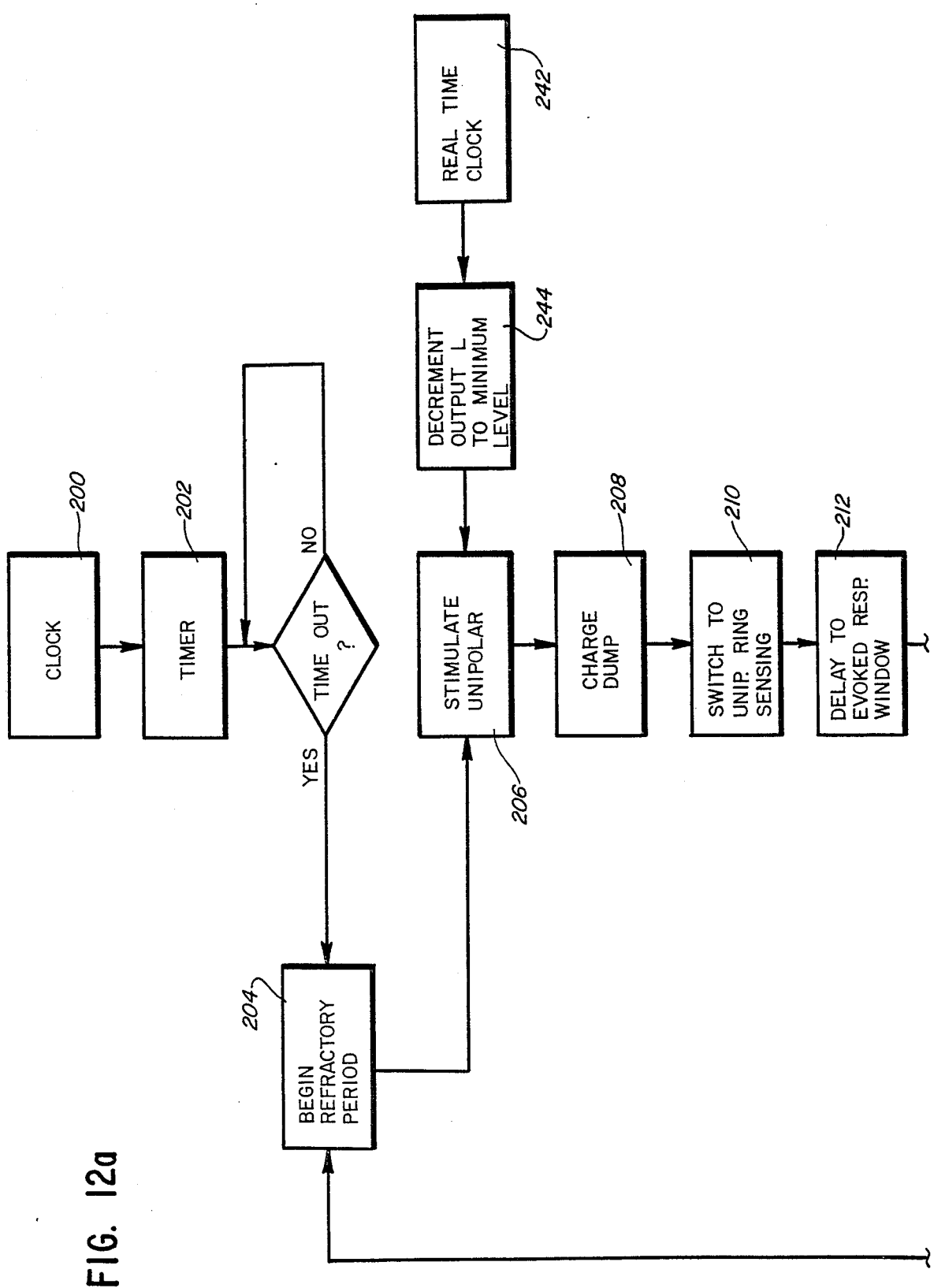

A flow chart illustrating an operation of the circuit of FIG. 11 is presented as FIGS. 12a-12b.

Referring to FIGS. 12a and 12b, the operation of the system is as follows. Clock 200 will operate timer 202 which, when timed out, will begin a refractory period 204 and issue a stimulation pulse in a unipolar manner 206. Charge dump will occur 208 and the system will switch to unipolar ring sensing 210. A delay will occur to the evoked response window 212, and the window timer will then begin 214. Evoked response sensing will be enabled 216. If an evoked response is sensed 218, the response sensing will then be disabled 220 and the system will switch to bipolar sensing 222. On the other hand, if an evoked response is not sensed 218, the system will determine if the response window has ended 224, and once the window has ended without sensing a response, a stimulating backup pulse 226 will issue. The stored stimulus value will then be incremented 228. The response sensing will then be disabled 220, and the system will switch to bipolar sensing 222.

Once this system switches to bipolar sensing 222, the system will determine if the refractory period has ended 230. If the refractory period has ended, the alert sensing will be enabled 232. The system will sense for a natural R wave 234, and if an R wave is sensed, the timer will be reset 236, and a new refractory period will begin 238. If an R wave is not sensed by the end of the alert sensing period 240, a new refractory period will begin 204, and a stimulation will issue in a unipolar manner 206.

The stimulation pulse which is issued in the unipolar manner 206 is also controlled by a real time clock 242 which decrements the output level L to a minimum level 244 at selected intervals. The selected intervals could be any selected amount of time, perhaps every twelve hours, or every hour, or every fifteen minutes, etc. At these selected intervals, if an evoked potential is not sensed in response to the lowest level of stimulation, a stimulus at the highest output level M occurs. The stored (now lowest level of) output stimulation is then incremented to the next highest level, and should this incremented output level not evoke a response at the next cycle, the output stimulus level is again incremented.

It is preferred that the timer be reset every time a stimulation backup pulse is issued 226. If the timer were not reset, every time a stimulation pulse at a maximum level is issued there will be a variation in the interval between stimuli as read by the cardiologist on an ECG. If the timer is reset 246, after each stimulation with a backup pulse 226, the interval between the maximum output stimulus and the subsequent stimuli will remain constant.

The above has been offered for illustration purposes only, and is not intended to limit the scope of the invention of this application, which is as defined in the claims below.

That which is claimed is:

1. The method of cardiac pacing and sensing which comprises the steps of:
   providing a cardiac pacing lead having a first electrode carried on the distal end of said lead and a second electrode carried by the lead and spaced from said first electrode and free of electrical connection thereto;
   positioning said lead in a heart chamber;
   periodically emitting an electrical stimulus, pulse in a unipolar mode, from said first electrode to stimulate cardiac muscular contraction; and
   detecting in a unipolar mode, an electric potential response evoked by said pulse, by said second electrode, whereby signal interference caused by residual polarization of said first electrode is suppressed.

2. The method of claim 1 in which said pacer lead connects to pacer power and circuit means sealed in a metal can, said metal can serving as reference electrode to said first and second electrodes.

3. The method of claim 1 in which, following said pulse, an output capacitor is discharged through the heart muscle for 5 to 15 milliseconds to cause residual charge to depart said first electrode.

4. The method of claim 1 in which pairs of said first and second electrodes are carried on separate lead sections, said electrode pairs being all in electrical communication with pacer power and circuit means sealed in a metal can, said metal can serving as a reference electrode to said first and second electrodes, one of said pairs of electrodes being installed in an atrium and another pair in a ventricle.

5. The method of claim 1 in which said first and second electrodes are spaced at least about 0.5 cm. apart.

6. The method of cardiac pacing and sensing which comprises the steps of:
providing a cardiac pacing lead having a first electrode carried on the distal end of said lead and a second electrode carried by the lead and spaced from said first electrode and free of electrical connection thereto;
positioning said lead in a heart chamber;
periodically emitting an electrical stimulus pulse from said first electrode to stimulate cardiac muscular contraction and
detecting, in a unipolar mode, an electric potential response evoked by said pulse, by said second electrode, whereby signal interference caused by residual polarization of said first electrode is suppressed;
said second electrode being activated at a predetermined time interval after said electrical stimulus, the duration of said activation being about 10 to 50 milliseconds, whereby said evoked response can be detected and selected from other heart electrical activity.

7. The method of claim 6 in which, at a predetermined interval before said electrical stimulus pulse and while the evoked response is not being detected, a circuit is activated including said first and second electrodes in bipolar relation to identify heart electrical activity associated with heartbeat generation, and emission of said electrical stimulus pulse is inhibited upon sensing of said heart electrical activity.

8. A method of cardiac pacing and sensing which comprises providing a cardiac pacing lead having a first electrode carried on the distal end of said lead and a second electrode carried by the lead and spaced from said first electrode and free of electrical connection thereto, said second electrode being in the form of a ring carried by said lead and being spaced at least about 0.5 cm from said first electrode, periodically emitting an electrical stimulus pulse in a unipolar mode, from said first electrode positioned in a heart chamber to stimulate cardiac muscular contraction, and detecting an electric potential response evoked by said pulse, in a unipolar mode, by said second electrode, whereby signal interference caused by residual polarization of said first electrode is suppressed.

9. The method of claim 8 in which said pacer lead connects to pacer power and circuit means sealed in a metal can, said metal can serving as a reference electrode to said first and second electrodes.

10. The method of claim 9 in which following said pulse, an output capacitor is discharged through the heart muscle for 5 to 15 milliseconds to cause residual charge to depart said first electrode.

11. The method of claim 9 in which an evoked response sensing circuit including said second electrode is activated at a predetermined time interval after said electrical stimulus pulse, the duration of said activation being about 10 to 50 milliseconds, whereby said evoked response can be detected and selected from other heart electrical activity.

12. The method of cardiac pacing and sensing which comprises providing a cardiac pacing lead having a first electrode carried on the distal end of said lead and a second electrode carried by the lead and spaced from said first electrode and free of electrical connection thereto, said second electrode being in the form of a ring carried by said lead and being spaced at least about 0.5 cm from said first electrode, periodically emitting an electrical stimulus pulse from said first electrode on a cardiac pacer lead positioned in a heart chamber to stimulate cardiac muscular contraction, detecting an electric potential response evoked by said pulse, by said second electrode, whereby signal interference caused by residual polarization of said first electrode is suppressed; providing pacer power and circuit means sealed in a metal can and serving as a reference electrode to said first and second electrodes; providing an evoked response sensing circuit including said second electrode, activating said second electrode at a predetermined time interval after said electrical stimulus pulse, the duration of said activation being about 10 to 50 milliseconds, whereby said evoked response can be detected and selected from other heart electrical activity; activating a circuit to identify heart electrical activity associated with hearbeat generation, and inhibiting the emission of a subsequent electrical stimulus upon sensing of said heart electrical activity.

13. The method of claim 12 in which said first electrode emits said pulse and the second electrode detects said evoked response in unipolar mode.

14. The method of claim 12 in which pairs of first and second electrodes are carried on separate lead sections, said electrode pairs being all in electrical communication with pacer power and circuit means sealed in a metal can, said metal can serving as a reference electrode to said first and second electrodes.

15. The method of claim 14 in which one of said pairs of electrodes is for atrial installation and another pair is for ventricular installation.

16. The method of cardiac pacing and sensing which comprises providing a cardiac pacing lead having a first electrode carried on the distal end of said lead and a second electrode carried by the lead and spaced from said first electrode and free of electrical connection thereto; positioning said lead in a heart chamber; periodically emitting an electrical stimulus pulse from said first electrode to stimulate cardiac muscular contraction, said electrical stimulus pulse being emitted from the first electrode in unipolar mode;
sensing the evoked response from the heart muscle by the second electrode in unipolar mode during a predetermined window of time subsequent to said emitting of the pulse of electrical potential;
prior to emitting said electrical stimulus pulse from a first electrode, sensing for electrical signals indicating natural heart contraction in bipolar mode using the first and second electrodes during a predetermined alert period preceding the emission of said electrical stimulus pulse by the first electrode, and if said electrical activity signifying natural heart contraction is sensed, inhibiting the emission of the electrical stimulus pulse.

17. The method of claim 16 in which a third electrode is provided to serve as a reference electrode for the first and second electrodes during emission of the electrical stimulus pulse and during sensing of the evoked response.

18. The method of claim 17 in which pacer power and circuit means are provided sealed in a metal can, said metal can serving as said reference electrode for said first and second electrodes during the emissions of the electrical stimulus pulse and during the sensing of the evoked response.

19. The method of claim 18 in which said first electrode is carried on the distal end of said cardiac pacer lead, and the second electrode is in the form of a ring carried about said lead.

20. The method of claim 19 in which, following said electrical stimulus pulse, an output capacitor is discharged through the heart muscle for 5 to 15 milliseconds to cause residual charge to depart said first electrode.

21. The method of claim 20 in which pairs of first and second electrodes are carried on separate lead sections, said electrode pairs being all in electrical communication with said pacer power and circuit means, one of said pairs of electrodes being installed in an atrium and the other being installed in the ventricle.

22. The method of claim 21 in which said first and second electrodes on a common lead are spaced at least about 0.5 cm. apart.

23. Apparatus for cardiac pacing and sensing which comprises:
a cardiac pacing lead adapted for positioning within a heart chamber, said lead having a first electrode on its distal end and a second electrode spaced from said first electrode;
means for transmitting to said first electrode an electrical stimulus pulse in a unipolar mode, to stimulate cardiac muscular contraction;
sensing means, coupled to said second electrode, for detecting an electric potential response evoked by said electrical stimulus pulse in a unipolar mode;
circuit means permitting said first electrode and said second electrode to be free of electrical connection between each other while transmitting said pulse and while sensing, whereby signal interference caused by residual polarization of said first electrode is suppressed.

24. The apparatus of claim 23 in which said second electrode is in the form of a ring carried about said cardiac pacing lead.

25. The apparatus of claim 23 in which pacer power and circuit means are provided in connection with said pacer lead, said pacer power and circuit means being sealed in a metal can, said metal can serving as a reference electrode to said first and second electrodes.

26. The apparatus of claim 23 in which output capacitor means and control means are provided to provide a discharge path through the heart muscle to intermittently permit residual charge to depart said first electrode.

27. Apparatus for cardiac pacing and sensing which comprises:
a cardiac pacing lead adapted for positioning within a heart chamber, said lead having a first electrode on its distal end and a second electrode spaced from said first electrode;
means for transmitting to said first electrode an electrical stimulus pulse to stimulate cardiac muscular contraction;
sensing means, coupled to said second electrode, for detecting, in a unipolar mode, an electric potential response evoked by said electrical stimulus pulse;
circuit means permitting said first electrode and said second electrode to be free of electrical connection between each other while transmitting said pulse and while sensing, whereby signal interference caused by residual polarization of said first electrode is suppressed;
said sensing means including means for activation thereof at a predetermined time interval after activation of the means for transmitting to the first electrode an electrical stimulus pulse and for limiting the duration of activation of said sensing means to about 10 to 50 milliseconds, whereby said evoked response can be detected and selected from other heart electrical activity.

28. The apparatus of claim 23 including means for detecting heart electrical activity associated with heart muscle contraction, and means for inhibiting said transmitting means upon sensing of said heart electrical activity.

29. The apparatus of claim 23 having a plurality of said pairs of first and second electrodes carried on separate lead sections, said electrode pairs all being in electrical communication with pacer power and circuit means, and reference electrode means provided in electrical communication with said first and second electrodes.

30. The apparatus of claim 29 in which said reference electrode means is a metal can which carries said pacer power and circuit means.

31. Apparatus for cardiac pacing and sensing which comprises:
a cardiac pacing lead adapted for positioning within a heart chamber, said lead having a first electrode on its distal end and a second electrode in the form of a ring spaced from said first electrode;
pacer power and circuit means connected to said pacer lead, and including means for transmitting to said first electrode an electrical stimulus pulse in the unipolar mode to stimulate cardiac muscular contraction;
sensing means coupled to said second electrode, for detecting in a unipolar mode an electric potential response evoked by said pulse; and
circuit means permitting said first electrode and said second electrode to be free of electrical connection between each other while transmitting said pulse and while sensing, whereby signal interference caused by residual polarization of said first electrode is suppressed.

32. The apparatus of claim 31 in which a third electrode is provided to serve as a reference electrode to said first and second electrodes.

33. The apparatus of claim 32 including means for detecting heart electrical activity associated with heart muscle contraction, and means for inhibiting said transmitting means upon sensing of said heart electrical activity.

34. Apparatus for cardiac pacing and sensing which comprises:
a cardiac pacing lead adapted for positioning within a heart chamber, said lead having a first electrode on its distal end and a second electrode in the form of a ring spaced from said first electrode;
pacer power and circuit means provided in connection with said pacer lead, and including means for transmitting to said first electrode an electrical stimulus pulse in a unipolar mode to stimulate cardiac muscular contraction;

sensing means coupled to said electrode, for detecting in a unipolar mode an electric potential response evoked by said pulse;

circuit means permitting said first electrode and said second electrode to be free of electrical connection between each other while transmitting said pulse and while sensing, whereby signal interference caused by residual polarization of said first electrode is suppressed;

means for detecting heart electrical activity associated with heart muscle contraction; means for inhibiting said transmitting means upon sensing of said heart electrical activity;

said sensing means including means for activation thereof at a predetermined time interval after activation of the transmitting means, and for limiting the duration of activation of said sensing means to about 10 to 50 milliseconds, whereby said evoked response can be detected and selected from other heart electrical activity.

35. The apparatus of claim 34 in which output capacitor means and control means are provided to provide a discharge path through the heart muscle to intermittently permit residual charge to depart said first electrode after transmitting to the first electrode an electrical stimulus.

36. The apparatus of claim 35 in which said pacer power and circuit means is carried in a metal can, said metal can also serving as said reference electrode means.

37. The apparatus of claim 36 having a plurality of said pairs of first and second electrodes, said electrode pairs being all in electrical communication with said pacer power and circuit means.

38. The apparatus of claim 37 in which one of said pairs of electrodes is for atrial installation and another pair is for ventricular installation.

39. The apparatus of claim 38 in which said first and second electrodes are spaced at least about 0.5 cm. apart.

40. Apparatus for cardiac pacing and sensing which comprises:

a cardiac pacing lead adapted for positioning within a heart chamber, said lead having a first electrode on its distal end and a second electrode spaced from said first electrode;

means for transmitting to said first electrode an electrical stimulus pulse in a unipolar mode, to stimulate cardiac muscular contraction.

sensing means, coupled to said second electrode, for detecting an electric potential response evoked by said electrical stimulus pulse in a unipolar mode;

circuit means permitting said first electrode and said second electrode to be free of electrical connection between each other while transmitting said pulse and while sensing, whereby signal interference caused by residual polarization of said first electrode is suppressed;

pacer power means;

one of said pairs of electrodes being for atrial installation and another pair of electrodes being for ventricular installation; and said first and second electrodes being spaced at least about 0.5 cm. apart.

* * * * *